(12) United States Patent
Brgles et al.

(10) Patent No.: US 10,597,640 B2
(45) Date of Patent: Mar. 24, 2020

(54) ELUTION MOBILE PHASE AND PROCESS FOR IMMUNOAFFINITY CHROMATOGRAPHY OF VIRUSES

(71) Applicants: SVEUCILISTE U ZAGREBU, Zagreb (HR); BIA SEPARATIONS D.O.O., Adjovscina (SI)

(72) Inventors: Marija Brgles, Zagreb (HR); Beata Halassy, Zagreb (HR); Dubravko Forcic, Zagreb (HR)

(73) Assignees: Sveuciliste U Zagrebu, Zagreb (HR); Bia Separations d.o.o., Adjovscina (SI)

( * ) Notice: Subject to any disclaimer, the term of this patent is extended or adjusted under 35 U.S.C. 154(b) by 0 days.

(21) Appl. No.: 16/072,290

(22) PCT Filed: Jan. 17, 2017

(86) PCT No.: PCT/EP2017/050911
§ 371 (c)(1),
(2) Date: Jul. 24, 2018

(87) PCT Pub. No.: WO2017/129450
PCT Pub. Date: Aug. 3, 2017

(65) Prior Publication Data
US 2019/0032025 A1 Jan. 31, 2019

(30) Foreign Application Priority Data
Jan. 27, 2016 (HR) .............. P 20160086 A (51) Int. Cl.
*C12N 7/02* (2006.01)
*A61K 39/155* (2006.01)
*C12N 7/00* (2006.01)

(52) U.S. Cl.
CPC .............. *C12N 7/00* (2013.01); *A61K 39/155* (2013.01); *C12N 7/02* (2013.01); *C12N 2760/18031* (2013.01); *C12N 2760/18051* (2013.01)

(58) Field of Classification Search
None
See application file for complete search history.

(56) References Cited

U.S. PATENT DOCUMENTS 5,726,293 A 3/1998 Seed

FOREIGN PATENT DOCUMENTS

| EP | 1568710 B1 | 12/2009 |
|---|---|---|
| EP | 2583973 A1 | 4/2013 |
| EP | 2361975 B1 | 12/2014 |
| JP | 2003176111 A | 6/2003 |
| JP | 2005206602 A | 8/2005 |
| JP | 2015020955 A | 2/2015 |
| WO | 9407912 A1 | 4/1994 |
| WO | 2008031020 A2 | 3/2008 |
| WO | 2015176006 A2 | 11/2015 |

OTHER PUBLICATIONS

Arakawa et al., Elution of antibodies from a Protein-A column by aqueous arginine solutions, Protein Expression and Purification 36 (2004) 244-248.
Banjac et al., Purification of Vero cell derived live replication deficient influenza A and B virus by ion exchange monolith chromatography, Vaccine 32 (2014) 2487-2492.
Burgess et al., Advances in gentle immunoaffinity chromatography, Curr. Opin. Biotechnol. 13 (2002) 304-308.
Carr et al., Nanoparticle Tracking Analysis a Review of Applications and Usage 2010-2012, NanoSight Ltd. 2013, 193 pages.
Durkee et al., Immunoaffinity Chromatographic Purification of Russell's Viper Venom Factor X Activator Using Elution in High Concentrations of Magnesium Chloride, Protein Expression and Purification 4 (1993) 405-411.
Ehresmann et al., Spectrophotometric Determination of Protein Concentration in Cell Extracts Containing tRNA's and rRNA's, Analytical Biochemistry 54 (1973) 454-463.
Forcic et al., Concentration and purification of rubella virus using monolithic chromatographic support, Journal of Chromatography B, 879 (2011) 981-986.
Gerster et al., Purification of infective baculoviruses by monoliths, Journal of Chromatography A, 1290 (2013) 36-45.
Halassy et al., Adjuvant activity of peptidoglycan monomer and its metabolic products, Vaccine 21 (2003) 971-976.
Halassy et al., Effectiveness of novel PGM-containing incomplete Seppic adjuvants in rabbits, Vaccine 25 (2007) 3475-3481.
Moser et al., Immunoaffinity chromatography: an introduction to applications and recent developments, Bioanalysis Apr. 2010; 2(4): 769-790.
Nestola et al., Improved Virus Purification Processes for Vaccines and Gene Therapy, Biotechnology and Bioengineering, vol. 112, No. 5, May 2015, 843-857.
Spoljar et al., Influence of adjuvant-active peptidoglycan monomer on specific T cell responses in mice, Vaccine 20 (2002) 3543-3550.
International Search Report issued in PCT/EP2017/050911 dated Apr. 5, 2017, 4 pages.
Written Opinion of the International Searching Authority issued in PCT/EP2017/050911 dated Apr. 5, 2017, 6 pages.

*Primary Examiner* — Stacy B Chen
(74) *Attorney, Agent, or Firm* — RatnerPrestia (57) ABSTRACT

The present invention discloses a novel composition of the elution mobile phase for virus purification by immunoaffinity chromatography which is consisting of one or more amino acids: L-serine, L-asparagine, or L-glutamine, or their salts with pharmaceutically acceptable acids; one or more auxiliary ingredients: L-arginine, glycine or imidazole, or their salts with pharmaceutically acceptable acids; one or more pharmaceutically acceptable pH adjusting agents for correcting the pH value of the mobile phase from pH=6.0-8.0; and purified water, up to 100% w/w of the mobile phase composition. The invention provides the use of immunoaffinity chromatography as a key step in the production of viral vaccines and/or viral vectors, in separation of infectious from non-infectious viral particles, and for enrichment of the viral suspension in infectious viral particles.

7 Claims, 2 Drawing Sheets

ELUTION MOBILE PHASE AND PROCESS FOR IMMUNOAFFINITY CHROMATOGRAPHY OF VIRUSES

CROSS REFERENCE TO RELATED APPLICATIONS

This application is the U.S. National Phase Application of PCT/EP2017/050911, filed Jan. 17, 2017, which claims priority to Croatian Patent Application No. P20160086A, filed Jan. 27, 2016, the contents of such applications being incorporated by reference herein.

TECHNICAL FIELD

The invention relates to a new elution mobile phase for downstream purification of viruses by immunoaffinity chromatography, preparation of this elution mobile phase, as well as the new process for purification of viruses using said mobile phase.

This purification process relates to the field of downstream purification of viruses from suspensions and solutions of complex compositions within highly efficient production of various high quality biotechnological preparations and medical immunobiological drugs based on live viruses and viral vectors.

Technical Problem

An aspect of the present invention solves the technical problem connected with immunoaffinity chromatography as powerful and highly selective technique, for purification of viable, infectious viruses and viral vectors.

Immunoaffinity chromatography is based on a highly specific and strong bond between antigen and antibody. The technical problem is that this bond cleavage can be usually realized only under very harsh elution conditions, e.g. at low or high pH, or by using high concentration solutions of chaotropic agents such as 8 M urea, 6 M guanidinium chloride, or 3 M potassium thiocyanate (KSCN) solutions.

In the same time, such conditions destroy immobilized proteins (specific antibody) bounded covalently on the chromatographic column, and most importantly destroy viruses (to be purified) as well as their infectivity. As a consequence, immunoaffinity chromatography is not suitable as general technique for isolation and purification of biologically active molecules, and especially not for viable viruses.

An aspect of the present invention opens the possibility of using the immunoaffinity chromatography under native, physiological conditions of pH value close to 7.4, which do not affect viral integrity and/or infectivity. In this manner an aspect of the present invention represents effective and rapid method for purification of viral particles, their concentration, as well as separation of infectious from non-infectious viral particles.

PREVIOUS STATE OF ART

An aspect of the present invention belongs to the field of downstream purification of viruses as is described in the literature reference 1:
1) P. Nestola, C. Peixoto, R. R. J. S. Silva, P. M. Alves, J. P. B. Mota, M. J. T. Carrondo: Improved virus purification processes for vaccines and gene therapy, *Biotechnol. Bioeng.* 112 (2015) 843-857, incorporated by reference herein.

The downstream virus purification represents roughly 70% of whole manufacturing costs of viral vaccines or viral vectors for gene therapy. In the same time, it is a key bottleneck of these manufacturing processes. The target is to purify the virus obtained in upstream (cultivation) part of the whole process from impurities such as nucleic acids, proteins, and other biomolecules originating from the cells in which the virus was cultivated. In the same time, the virus is purified from viral aggregates, empty capsids, and various molecules used in the production process like albumin from bovine serum, various enzymes, etc.

Major methods which are employed in downstream virus purification, ultrafiltration and diafiltration, are effective in virus concentration, but not highly selective for purification. Furthermore, density gradient ultracentrifugation is a technique which enables concentration and purification of virus but cannot be scaled-up to industrial level. Beside this, the yields are very low and the process requires a buffer displacement step after the ultracentrifugation.

Chromatography is the most powerful purification method. The ion-exchange chromatography at native conditions has been employed for purification of viruses, providing various yields depending on the type of the virus. The potential of the ion-exchange chromatography in virus purification has been increased after discovery and implementation of monolithic chromatographic carriers. However, the viruses with lipid capsid such as smallpox or mumps virus still represent chromatographic challenge. The success of virus purification by the use of ion chromatography is described in literature references 2-5:
2) M. Banjac, E. Roethl, F. Gelhart, P. Kramberger, B. Lah Jarc, M. Jarc, A. Štrancar, T. Muster, M. Peterka: Purification of Vero cell derived live replication deficient influenza A and B virus by ion exchange monolith chromatography, *Vaccine* 32 (2014) 2487-2492, incorporated by reference herein;
3) P. Gerster, E. M. Kopecky, N. Hammerschmidt, M. Klausberger, F. Krammer, R. Grabherr, C. Mersich, L. Urbas, P. Kramberger, T. Paril, M. Schreiner, K. Nobauer, E. Razzizi-Fazeli, A. Jungbauer: Purification of infective baculoviruses by monoliths. *J. Chromatogr. A* 1290 (2013) 36-45, incorporated by reference herein;
4) EP2361975 B1; M. Peterka, A. Strancar, M. Banjac, P. Kramberger, E. Maurer, T. Muster: Method for influenza vaccine purification; Bia Separations d.o.o. (SI) and Avir Green Hills Biotechnology Res. Dev. Trade AG (AT), incorporated by reference herein;
5) D. Forčić, M. Brgles, J. Ivancic-Jelecki, M. Šantak, B. Halassy, M. Barut, R. Jug, M. Markušić, A. Štrancar: Concentration and purification of rubella virus using monolithic chromatographic support, *J. Chromatogr. B* 879 (2011) 981-986, incorporated by reference herein.

Immunoaffinity chromatography which is based on the use of immobilized antibodies in affinity chromatography is one of the most powerfull techniques in protein purification. Thanks to high specificity of antigen-antibody interaction, it is possible to achieve high degree of purification (even 1000×) and concentration in a single step. General knowledge of immunoaffinity chromatography can be, for instance, teached from the literature reference 6:
6) A. C. Moser, D. S. Hage: Immunoaffinity chromatography: an introduction to applications and recent developments, *Bioanalysis* 2 (2010) 769-790, incorporated by reference herein.

The great disadvantage of this chromatographic technique is that the elution of such molecules requires very harsh conditions to cleave antigen-antibody bonds, but this results also in disruption of intramolecular bonds. Such conditions are destructive for both immobilized antibody as well as for targeted proteins (antigen), especially for viruses. This is the reason why this method is barely employed for virus purification and concentration.

Some examples of milder elution solutions in immunoaffinity chromatography are as follows:
(i) highly concentrated magnesium chloride ($MgCl_2$) solution as described in literature reference 7;
(ii) "Gentle Elution Buffer" of the Thermo Scientific Company, a buffer of unknown proprietary composition, which is obviously based on highly concentrated aqueous solution of certain salts of almost neutral pH value; and
(iii) elution buffer based on polyol plus sodium chloride (NaCl) solution as disclosed in literature reference 8;
7) K. H. Durkee, B. H. Roh, G. J. Doellgast: Immunoaffinity chromatographic purification of Russell's viper venom factor X activator using elution in high concentrations of magnesium chloride, *Protein Expr. Purif.* 4 (1993) 405-411, incorporated by reference herein;
8) R. R. Burgess, N. E. Thompson: Advances in gentle immunoaffinity chromatography, *Curr. Opin. Biotechnol.* 13 (2002) 304-308, incorporated by reference herein.

However, highly concentrated solutions of salts often have negative impact on virus infectivity. In the same time a prerequisite of the use of polyol-depending antibodies is selection and production of monoclonal antibodies. After such step, the removal of the salt and polyol is essential. All these disadvantages decrease their practical use in immunoaffinity chromatography in purification of infectious viruses.

The use of amino acids as elution reagents in corresponding mobile phases for elution in affinity chromatography has been described; see literature references 9 and 10:
9) T. Arakawa, J. S. Philo, K. Tsumoto, R. Yumioka, D. Ejima: Elution of antibodies from a Protein-A column by aqueous arginine solutions, *Prot. Expr. Purif.* 36 (2004) 244-248, incorporated by reference herein.
10) JP 2005206602 A; R. Yumioka, D. Ejima, R. Arakawa: Purification method for preventing degeneration of antibody; Ajinomoto Co. Inc. (JP), incorporated by reference herein.

Thus arginine (Arg) was employed for elution of antibodies from the protein A column, but only in combination with acidic pH. Herein, the elution is predominantly realized by the low pH which results in cleavage of hydrogen bonds in protein-protein interactions i.e. in this case antigen-antibody interactions, but also intramolecular hydrogen bonds resulting in denaturation of the immobilized protein and the biomolecule to be purified. The arginine addition just enhances an efficacy of low pH elution.

Document WO 2008/031020A2, incorporated by reference herein, discloses the use of L-arginine as a key ingredient of the mobile phase for both wash of nespecifically bound impurities to affinity column in purification of antibodies via affinity chromatography, as well as for elution of pure antibodies, in the final elution step. Arginine was used at concentrations from 0.1-2 M at pH=4.5-8.0 in the washing step, and at pH=2.0-4.0 in the elution step; see literature reference 11.
11) WO 2008/031020 A2; S. Sun, C. Gallo: Arginine wash in protein purification using affinity chromatography; Wyeth Corp. (US), incorporated by reference herein.

Tanaka and co-workers described the composition of the mobile phase and the process for purification of proteins (antibodies) by immunoaffinity chromatography with immobilized Fc binding protein. The mobile phase was of the following composition:
(i) aminoacids: L-arginine, L-proline, L-threonine, and L-histidine; at concentrations from 0.1-3.5 M;
(ii) imidazole (Imi); at concentrations from 0.1-3 M;
(iii) urea;
(iv) buffer, of pH value from 3.9-5.0; and
(v) aqueous ethanol (EtOH)/water mixture with 5-50% EtOH; as a solvent; up to 100% of the mobile phase composition; see literature reference 12:
12) JP 2015020955 A; T. Tanaka, T. Ide: Eluate for antibody purification and antibody purification method using eluate concerned; Tosoh Corp. (JP), incorporated by reference herein.

Closely similar to amino acids, compounds which can act as certain amino acids mimetics have been described as effective eluting reagents. In this manner U.S. Pat. No. 5,726,293 A, incorporated by reference herein, discloses the use of imidazole as histidine analogue to be effective eluting agent in immunoaffinity chromatography of proteins; see literature references 13 and 14.
13) U.S. Pat. No. 5,726,293 A; B. Seed: Affinity purification methods involving imidazole elution; The General Hospital Corp. (US), incorporated by reference herein.

Also, WO 94/07912 A1, incorporated by reference herein, teaches that guanidinium salts as arginine, alkylamines as lysine, aliphatic carboxylic acids as glutamate and aspartate mimetic agents, as well as earlier mentioned imidazole as histidine mimetic, can be employed as effective eluting reagents for mobile phases in immunoaffinity chromatography of proteins; see literature reference 14:
14) WO 94/07912 A1; B. Seed: Affinity purification methods involving amino acid mimetics as elution reagents; The General Hospital Corp. (US), incorporated by reference herein.

According to our best knowledge the latter two documents represent the closest prior art to an aspect of the present invention. In the same time, the composition of the elution mobile phase from an aspect of the present invention or any similar version as well as its use for purification of infectious viruses via immunoaffinity chromatography have not been disclosed in any of either patent or non-patent literature.

SUMMARY OF THE INVENTION

An aspect of the present invention discloses the composition of the elution mobile phase for purification and concentration of viruses via immunoaffinity chromatography, the process for performing such chromatographic purification, and its use.

The elution mobile phase from the present is an aqueous solution consisting of:
(i) one or more amino acids;
(ii) one or more ingredients: L-arginine, glycine (Gly), imidazole, or their salts with pharmaceutically acceptable acids.
(iii) one or more pharmaceutically acceptable pH adjusting agents, acid or base, for correcting the pH value of the mobile phase to pH=6.0-8.0; and
(iv) purified water; up to 100% w/w of the mobile phase composition; wherein the amino acids are selected from: L-serine (Ser), L-asparagine (Asn), L-glutamine (Gln), or their salts with pharmaceutically acceptable acids. Preferably, the amino acid is L-serine.

In the composition from an aspect of the present invention the amino acid is used at concentrations from 0.1-2 M, preferably at 0.75-1.5 M. The further ingredient under paragraph (ii) is used at concentrations from 0.1-2 M, preferably at 0.75-1.5 M. The optimal pH value of the mobile phase from an aspect of the present invention is pH=6.0-8.0, preferably from pH=7.2-7.4.

The process for virus isolation and purification via immunoaffinity chromatography is consisting of the following steps:
(i) binding the antibody to the chromatographic stationary phase; the antibody is specific for a surface protein of the virus which will be subjected to the said purifying process; the binding is realized by conventional techniques of covalent binding which results in formation of the column for immunoaffinity chromatography;
(ii) then the said chromatographic column from the step (i) is:
  (a) equilibrated by flushing it with the solution of binding buffer consisting of: 20 mM of 3-(N-morpholino) propanesulfonic acid, 0.15 M sodium chloride at pH=7.2-7.4; followed by
  (b) loading of the starting suspension of contaminated viruses which is intended to be purified onto such equilibrated chromatographic column;
(iii) washing of contaminants and non-bonded viruses out of the column by flushing it with the same above-mentioned binding buffer;
wherein,
(iv) elution of the purified virus bounded on the stationary phase of the column is realized by the use of the elution mobile phase from an aspect of the present invention, yielding an eluate in the form of a suspension of purified virus in said mobile phase.

Thus obtained suspension of purified virus can be subsequently used for further preparation of any conventional type of viral preparations, e.g. viral vaccines, etc, as is known to the person skilled in the art of pharmaceutical technology and biotechnology.

The elution mobile phase according from an aspect of the present invention is used for purification and/or concentration of viruses by immunoaffinity chromatography.

The viruses that can be subjected to purification and concentration via immunoaffinity chromatography by using the mobile phase from an aspect of the present invention are selected from the group comprising:
(a) Avulaviruses: Newcastle disease virus;
(b) Morbilliviruses: measles virus;
(c) Respiroviruses: human parainfluenza virus 1, human parainfluenza virus 3, Sendai virus;
(d) Rubulaviruses: human parainfluenza virus 2, human parainfluenza virus 4, mumps virus, parainfluenza virus 5;
(e) Metapneumoviruses: human metapneumovirus; and
(f) Orthopneumoviruses: human respiratory syncytial virus.

Preferably the mobile phase is used for purification and concentration of the viruses selected from the group consisting of: mumps virus, measles virus, and other viruses from the family of Paramyxoviridae.

In another embodiment of this invention, the mobile phase is employed for purification and separation of infectious from non-infectious viral particles by immunoaffinity chromatography. In this manner, an aspect of the present invention enables preservation of infectivity of viruses what can be hardly achieved by the use of any alternative processes from the state of the art.

Additionally, the mobile phase from an aspect of the present invention is employed for purification of viral vectors.

DETAILED DESCRIPTION

An aspect of the present invention discloses a novel composition of the mobile phase for purification and concentration of viruses via immunoaffinity chromatography, the process for performing such chromatographic purification, and its use.

The mobile phase from the present is an aqueous solution consisting of:
(i) one or more amino acids;
(ii) one or more ingredients: L-arginine, glycine, imidazole, or their salts with pharmaceutically acceptable acids.
(iii) one or more pharmaceutically acceptable pH adjusting agents, acid or base, for correcting the pH value of the mobile phase to pH=6.0-8.0; and
(iv) purified water; up to 100% w/w of the mobile phase composition; wherein the amino acids are selected from: L-serine (1), L-asparagine (2), L-glutamine (3), or their salts with pharmaceutically acceptable acids. Preferably, the amino acid is L-serine.

Beside free amino acids, they can be used in the form of their salts with non-toxic pharmaceutically acceptable acids selected from the group comprising hydrochloric acid, sulphuric acid, nitric acid, phosphoric acid, methanesulfonic acid, benzenesulfonic acid, p-toluenesulfonic acid, acetic acid, propionic acid, butyric acid, lactic acid, citric acid, malic acid, succinic acid, fumaric acid, maleic acid, tartaric acid, adipic acid, or their mixtures.

In the composition from an aspect of the present invention the amino acid is used at concentrations from 0.1-2 M, preferably at 0.75-1.5 M.

The ingredient from paragraph (ii) is used at concentrations from 0.1-2 M, preferably at 0.75-1.5 M.

Relative molar ratio (n/n) of amino acids L-serine, L-asparagine, L-glutamine, or their various mixtures, versus auxiliary ingredients L-arginine, glycine, imidazole, or their various mixtures can be from 10:1 to 1:10, preferably 3:1 to 1:3, and most preferably 1:1.

The pH adjusting agent can be either acid or base. Acid and base are selected from the group comprising: hydrochloric acid (HCl), sulfuric acid ($H_2SO_4$), sodium hydroxide (NaOH), and potassium hydroxide (KOH), or other pharmaceutically acceptable strong acids and bases.

The optimal pH value of the mobile phase from an aspect of the present invention is pH=6.0-8.0, preferably from pH=7.2-7.4.

The process for virus isolation and purification via immunoaffinity chromatography is consisting of the following steps:
(i) binding the antibody to the chromatographic stationary phase; the antibody is specific for a surface protein of the virus which will be subjected to the said purifying process; the binding is realized by conventional techniques of covalent binding which results in formation of the column for immunoaffinity chromatography;
(ii) then the said chromatographic column from the step (i) is:
  (a) equilibrated by flushing it with the solution of binding buffer consisting of: 20 mM of 3-(N-morpholino) propanesulfonic acid, 0.15 M sodium chloride at pH=7.2-7.4; followed by
  (b) loading of the starting suspension of contaminated viruses which is intended to be purified onto such equilibrated chromatographic column;
(iii) washing of contaminants and non-bonded viruses out of the column by flushing it with the same above-mentioned binding buffer;
wherein,
(iv) elution of the purified virus bounded on the stationary phase of the column is realized by the use of the elution mobile phase from an aspect of the present invention, yielding an eluate in the form of a suspension of purified virus in said mobile phase.

Thus obtained suspension of purified virus can be subsequently used for further preparation of any conventional type of viral preparations, e.g. viral vaccines, etc, as is known to the person skilled in the art of pharmaceutical technology and biotechnology.

An aspect of the invention provides the use of immunoaffinity chromatography as a key step in production of viral vaccines and/or viral vectors, with special focus on the fact that this process avoids common purification step of removing elution reagents, since amino acids are proved stabilizing agents in many existing vaccines. Additionally an aspect of the invention can be employed for separation of infectious from non-infectious viruses, what actually means enrichment of the viral suspension with the infective particles.

Initial Study of Immunoaffinity Chromatography Mobile Phase Development on Ovalbumin (OVA) as a Model Substance for Purification An initial study of efficacy of the mobile phase from an aspect of the present invention for immunoaffinity chromatography purification was performed with ovalbumin (OVA) as a model substance. For this study immunoaffinity column stationary phase was prepared by binding of OVA-specific polyclonal rabbit antibodies of IgG-class.

The latter were obtained by active immunization of rabbit with OVA formulated with commercially available oil adjuvant Montanide ISA720 (Seppic; Puteaux, France) and experimental adjuvant called peptidoglycan monomer (PGM; Pliva; Zagreb, Croatia). The latter was described in the literature references 15 and 16, whilst the adjuvant activity of this particular combination of Montanide ISA720 and PGM was disclosed in the literature reference 17:

15) B. Halassy Špoljar, T. Čimbora, I. Hanzl-Dujmović, B. Dojnović, A. Sabioncello, M. Krstanović, J. Tomašić: Influence of adjuvant-active peptidoglycan monomer on specific T cell responses in mice, *Vaccine* 20 (2002) 3543-3550, incorporated by reference herein;

16) B. Halassy, M. Krstanović, R. Frkanec, J. Tomašić: Adjuvant activity of peptidoglycan monomer and its metabolic products, *Vaccine* 21 (2003) 971-976, incorporated by reference herein;

17) B. Halassy, V. Vdović, L. Habjanec, M. Lang Balija, B. Gebauer, A. Sabioncello, T. Šantek, J. Tomašić: Effectiveness of novel PGM-containing incomplete Seppic adjuvants in rabbits, *Vaccine* 25 (2007) 3475-3481, incorporated by reference herein.

Antibodies from the rabbit serum were separated by chromatography and bound on the chromatographic column derived with active epoxy-groups yielding the chromatographic column for immunoaffinity chromatography, see Example 1.

Thus obtained immunoaffinity column, functionalized with the antibodies, was equilibrated with the binding buffer, an aqueous solution consisting of 20 mM 3-(N-morpholino) propanesulfonic acid (MOPS) and 0.15 M sodium chloride (NaCl) of pH=7.3. To thus equilibrated column, the samples of ovalbumin of 1 mg/mL were applied. Then, the column was washed with the binding buffer.

Optionally, beside MOPS, the key buffering substance in the binding buffer is one or more substances selected from the group comprising: 2-(N-morpholino)ethanesulfonic acid (MES); piperazine-N,N'-bis(2-ethanesulfonic acid) (PIPES); N-[tris(hydroxymethyl)methyl]-2-amino ethanesulfonic acid (TES); 2-[4-(2-hydroxyethyl)piperazine-1-yl]-ethanesulfonic acid (HEPES); 2-hydroxy-3-[tris(hydroxymethyl)methyl amino]-1-propanesulfonic acid (TAPSO); N-[tris(hydroxymethyl) methyl]glycine (Tricine); tris(hydroxymethyl)methylamine (Tris); or other pharmaceutically acceptable buffers which can generate the optimal pH value of 6.0-8.0.

After washing with the binding buffer, the column was subjected to elution with solutions of various tested amino acids whose pH values were corrected to pH=7.2-7.4 using solutions of pH adjusting agents such as 6 M aqueous solution of hydrochloric acid (HCl) or 2 M aqueous solution of sodium hydroxide (NaOH).

Final elution of most of remained OVA, which could not elute with the tested amino acids solutions, was performed with an aqueous solution of 20 mM glycine, 0.15 M NaCl at pH=2.3, which represents, so-called, non-native eluting conditions.

The following amino acids were tested: L-serine, L-serine+ L-arginine, L-serine+imidazole, L-serine+glycine (Gly) versus the alternative eluting reagents known in the prior art (therein used at acidic pH from 2.0 to 4.0; see literature reference 11): L-arginine, imidazole, glycine, and arginine+ imidazole. All mobile phases were corrected to native pH of 7.3.

Elution with 2 M NaCl solution was tested to check the level of elution without the effect of amino acid presence in the mobile phase.

Also, the elution with 20 mM Gly+0.15 M NaCl at pH=2.3 was examined for quantification of total elution of bound OVA at non-native pH value (of 2.3).

All experiments were carried out in triplicate. The results of this initial study with the model protein OVA are presented in Table 1, and shown in FIG. 1.

Detailed experimental procedures are described in Examples 1-3.

TABLE 1

Figure 1:
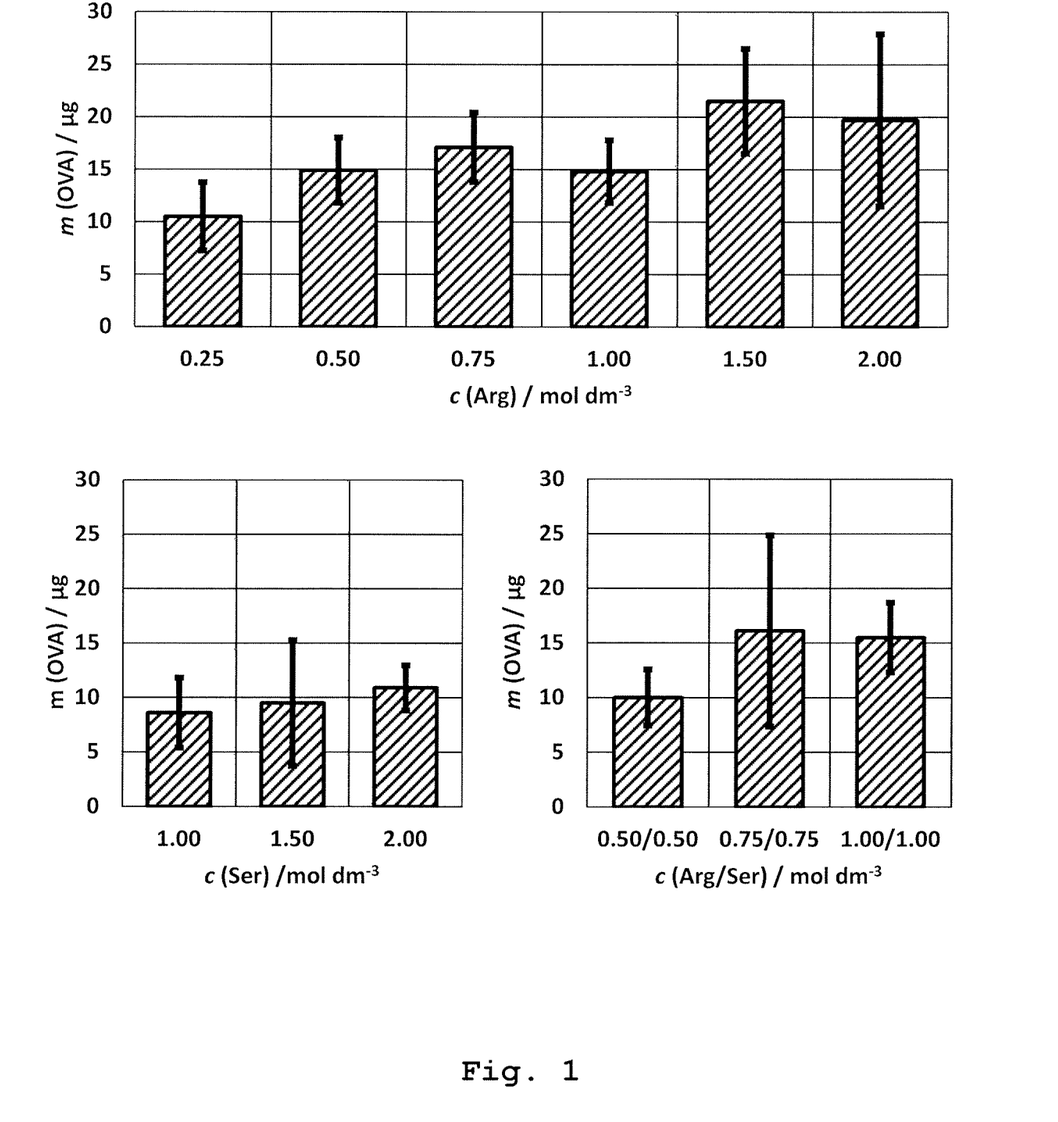
FIG. 1: Shows the efficacy of ovalbumin (OVA) elution via immunoaffinity chromatography by using different concentrations of amino acids L-arginine (Arg), L-serine (Ser) and their combination (Ser+Arg) in the elution mobile phase.

Efficacy of ovalbumin (OVA) elution with solutions of various amino acids by immunoaffinity chromatography; see also FIG. 1.[a]

| No. | Mobile phase[b] | Native elution at pH = 7.3[c] | | Non-native elution at pH = 2.3[d] | | Mass of total eluated OVA [µg][e] |
|---|---|---|---|---|---|---|
| | | Mass of OVA [µg][f] | Yield [%][g] | Mass of OVA [µg][h] | Yield [%][i] | |
| | Control elution: | | | | | |
| 1 | 2.0M NaCl | 14.7 ± 3.6 | 24 | 46.0 ± 4.1 | 76 | 60.7 |
| | The prior art-like elution: | | | | | |
| 2 | 1.5M Arg | 21.6 ± 4.9 | 34 | 41.8 ± 2.8 | 66 | 63.4 |
| 3 | 1.5M Gly | 11.7 ± 5.0 | 20 | 47.1 ± 3.2 | 80 | 58.8 |
| 4 | 1.5M Imi | 25.8 ± 2.9 | 42 | 35.4 ± 3.7 | 58 | 61.2 |
| | The present invention: | | | | | |
| 5 | 1.5M Ser | 7.8 ± 1.9 | 14 | 48.5 ± 3.9 | 86 | 56.3 |
| 6 | 0.75M Ser + 0.75M Arg | 16.8 ± 4.2 | 29 | 41.8 ± 6.6 | 71 | 58.6 |
| 7 | 0.75 Ser + 0.75M Imi | 17.5 ± 3.1 | 29 | 42.5 ± 1.2 | 71 | 60.0 |
| 8 | 0.75 Ser + 0.75 Gly | 7.9 + 1.7 | 14 | 47.7 ± 4.0 | 86 | 55.6 |
| | Elution at non-native (pH = 2.3) conditions: | | | | | |
| 9 | 20 mM Gly + 0.15M NaCl[j] | — | — | 57.5 ± 5.8 | 100 | 57.5 |

[a]Efficacy of the OVA elution with different amino acids-based mobile phases. The quantity [µg] of total bound OVA was determined by measuring the concentration of OVA in the fraction eluted at non-native conditions (pH = 2.3). The yields of elution at native (pH = 7.3) conditions were calculated against totally bound protein OVA. All experiments are performed in triplicate.
[b]pH values of all tested mobile phases were 7.3, except otherwise noted.
[c]Native elution represents the elution efficacy of mobile phases at physiological pH = 7.3.
[d]Non-native elution involves the elution at low, acidic value, pH = 2.3.
[e]Mass of total eluted OVA is a combined mass from native (pH = 7.3) and non-native (pH = 2.3) eluting conditions.
[f]Mass of OVA eluted at native conditions (pH = 7.3).
[g]Yield of OVA eluted at native conditions (pH = 7.3).
[h]Mass of OVA eluted at non-native conditions (pH = 2.3).
[i]Yield of OVA eluted at non-native conditions (pH = 2.3).
[j]pH value of this mobile phase was 2.3.

In this study the combination of L-serine with additional auxiliary ingredients from paragraph (ii) of the definition of the mobile phase such as L-arginine, imidazole, and glycine proved to be effective reagents for elution of the model protein OVA from the immunoaffinity chromatography column.

Serine (1) contains the hydroxyl (OH)-group which is known as a good hydrogen-bond both donor and acceptor. This can help in increasing efficacy of eluting power of the mobile phase as one can see from the results given in Table 1.

Due to significant similarity in hydrogen bond-forming ability between the OH group of L-serine and amide (CONH$_2$) group from L-asparagine (2) and L-glutamine (3), the latter two amino acids can be also alternatively used as eluting reagents in the mobile phase from an aspect of the present invention.

Both the high efficacy of the mobile phase from an aspect of the present invention and full preservation of the model protein OVA during the chromatographic process encouraged us for further study of this invention in a very demanding field of virus purification.

Study of Immunoaffinity Chromatography of Mumps Virus by Using the Mobile Phase from an Aspect of the Present Invention For this study the immunoaffinity chromatography column was prepared by binding of IgG-class of polyclonal guinea pig antibodies specific for the mumps virus. These antibodies were obtained by active immunization of guinea pigs with live attenuated vaccine L-Zagreb viral strain, grown in the culture of Vero cells. The virus is, before the immunization, purified by ultracentrifugation and formulated with commercially available oil adjuvant Montanide ISA206 and experimental peptidoglycan monomer (PGM) described in literature references 15-17; for experimental details see Example 4.

The antibodies from the guinea pig serum were isolated by chromatography and bound onto special stationary phase with free epoxy-groups; for experimental details see Example 4.

The chromatographic process was performed on ÄKTA-purifier 100 system equipped with UV-900 and pH/C-900 detectors (GE Healthcare; Uppsala, Sweden) at room temperature. Experimental details are described in the section "General remarks" and in the Example 4. The amounts of viruses in the samples were from $10^7$-$10^{10}$ CCID$_{50}$ at the sample size 30-150 mL of the starting viral suspension. In all cases, the immunoaffinity column was equilibrated with the binding buffer consisting of 20 mM 3-(N-morpholino)propanesulfonic acid (MOPS), 0.15 M NaCl at pH=7.2-7.4.

Optionally, the binding buffer can be formulated with alternative buffering substances selected from the group comprising: 2-(N-morpholino)ethanesulfonic acid; piperazine-N,N'-bis(2-ethane sulfonic acid); N-[tris(hydroxylmethyl)methyl]-2-aminoethane sulfonic acid; 2-[4-(2-hydroxyethyl)piperazine-1-yl]-ethane sulfonic acid; 2-hydroxy-3-[tris(hydroxymethyl)methylamino]-1-propanesulfonic acid; [tris(hydroxymethyl)methyl] glycine; tris (hydroxymethy methylamine; or other pharmaceutically acceptable buffers which can generate the optimal pH value of 6.0-8.0.

The elutions of the bound virus were carried out with various mobile phase solutions at the concentrations as defined earlier. The pH values were from 6.0-8.0, preferably from 7.2-7.4. The pH correction was conducted with acid or base as a pH adjusting agents, preferably with 2 M NaOH or 6 M HCl, as disclosed earlier.

After the native elution with the mobile phase from an aspect of the present invention, for additional removal of bound virus, 20 mM solution of glycine and 0.15 M NaCl was employed at non-native conditions (pH=2.3).

Elution with the mobile phase according to an aspect of the present invention proved to be effective for immunoaffinity chromatography of various viruses, for example, the vaccine L-Zagreb mumps viral strain, a kind of pleomorphic virus with lipid envelope of 200 nm average size.

The efficiency (the yield) of the chromatographic process was estimated against two parallel tests:
(i) determination of a half of infective dose; expressed as cell culture infective dose ($CCID_{50}$); and by
(ii) quantification of total viral particles by, so called, Nanoparticle Tracking Analysis (NTA); see the general procedure for the NTA analysis in the Section "General remarks".

Within this study almost all infective viral particles were eluted with the mobile phase containing amino acids, from either prior art-like or from an aspect of the present invention, under native conditions (pH=7.3), but the overall yield of the process expressed as combined count of infective particles in both "flow through" (FT) fractions and eluting fractions (E) was somewhat below the theoretical value. This suggests certain loss of virus during the chromatographic process, which was in the range of 20% of total viral particles or up to 50% of total infective viral particles.

The results are presented in the Table 2 and detailed experimental details are given in Examples 4 and 5.

TABLE 2

Efficacy of the elution in immunoaffinity chromatography within selected experimental examples by the use of the mobile phase from an aspect of the present invention, estimated by the amount of infective viral particles ($CCID_{50}$ test) and by the NTA test which measures the size and the count of all particles;[a] see also FIG. 2.

| No. | Sample | V [mL] | Ratio of size[b] | Total particles (by NTA)[c] | % of total particles[d] | $\log_{10}$ $CCID_{50}$[e] | % $CCID_{50}$[f] |
|---|---|---|---|---|---|---|---|
| | The prior art-like elution (but at pH = 7.3): E1 = 1.5M Arg elution reagent | | | | | | |
| 1 | load | 70 | 100 | $1.17 \cdot 10^{11}$ | — | 10.008 | — |
| | FT1 | 50 | 74 | $3.32 \cdot 10^{10}$ | 28.4 | 8.875 | 7.4 |
| | FT2 | 20 | 78 | $2.06 \cdot 10^{10}$ | 17.6 | 8.269 | 1.8 |
| | E1 | 6.5 | 100 | $3.84 \cdot 10^{10}$ | 32.8 | 9.631 | 42.0 |
| | E2 | 6 | 103 | $4.57 \cdot 10^{9}$ | 3.9 | 7.925 | 0.8 |
| | E3 | 4 | 90 | $2.81 \cdot 10^{9}$ | 2.4 | 7.242 | 0.2 |
| | Yield | — | — | — | 85.1 | — | 52.2 |
| 2 | load | 24 | 100 | $4.01 \cdot 10^{10}$ | — | 9.543 | — |
| | FT | 24 | 72 | $8.04 \cdot 10^{9}$ | 20.0 | 7.692 | 1.4 |
| | E1 | 6 | 105 | $1.95 \cdot 10^{10}$ | 48.6 | 9.432 | 77.4 |
| | E2 | 5 | 106 | $2.37 \cdot 10^{9}$ | 5.9 | 7.339 | 0.6 |
| | E3 | 4 | 79 | $1.13 \cdot 10^{9}$ | 2.8 | 5.512 | 0.01 |
| | Yield | — | — | — | 77.3 | — | 79.4 |
| | The present invention: E1 = 0.75M Ser + 0.75M Arg elution reagent | | | | | | |
| 3 | load | 70 | 100 | $1.46 \cdot 10^{11}$ | — | 9.613 | — |
| | FT1 | 50 | 86 | $3.76 \cdot 10^{10}$ | 25.8 | 8.443 | 6.8 |
| | FT2 | 20 | 85 | $1.90 \cdot 10^{10}$ | 13.0 | 8.283 | 4.7 |
| | E1 | 6 | 101 | $3.66 \cdot 10^{10}$ | 25.1 | 9.476 | 73.0 |
| | E2 | 5 | 104 | $3.56 \cdot 10^{9}$ | 2.4 | 8.323 | 5.1 |
| | E3 | 4 | 93 | $3.10 \cdot 10^{9}$ | 2.1 | n.d. | n.d. |
| | Yield | — | — | — | 68.4 | — | 89.6 |
| 4 | load | 25 | 100 | $5.20 \cdot 10^{10}$ | — | 9.166 | — |
| | FT | 25 | 70 | $1.27 \cdot 10^{10}$ | 24.4 | 6.889 | 0.5 |
| | E1 | 5.5 | 99 | $2.07 \cdot 10^{10}$ | 39.8 | 9.259 | 124.0 |
| | E2 | 5 | 97 | $2.20 \cdot 10^{9}$ | 4.2 | 7.727 | 3.6 |
| | E3 | 4 | 74 | $3.67 \cdot 10^{9}$ | 7.1 | n.d. | n.d. |
| | Yield | — | — | — | 75.5 | — | 128.1 |

Load = initial viral suspension;

FT = "flow through" fraction(s); fractions that contains material which do not undergo binding onto the stationary phase;

E1: fraction eluted with the mobile phase of at native (pH = 7.3) conditions;

E2: fractions eluted with 2M NaCl solution;

E3: fractions eluted under non-native (pH = 2.3) conditions with 20 mM Gly + 0.15M NaCl;

Yield was expressed as a percentage (%; w/w) of obtained viral count against the total used virus;

n.d. = not determined.

[a]Efficacy of the mumps virus elution with the amino acids-based mobile phases by immunoaffinity chromatography was determined through the test which measures the count of infective viruses, expressed as cell culture infective dose ($CCID_{50}$) as well as by the test of measuring of total viral count; this is called "Nanoparticle Tracking Analysis" (NTA); see the section "General remarks". All experiments are conducted in triplicate.

[b]The ratio of virus particles size in the given eluate fraction versus average viral particles size in the starting viral suspension.

[c]Viral particles count in the starting viral suspension (load) or in each given eluate fraction; as determined by the NTA.

[d]The percentage (%) of viral particles in a given eluate fraction versus the count in the starting viral suspension.

[e]Viral titer of infective particles; expressed as cell culture infective dose ($CCID_{50}$); in the starting viral suspension (load) and in each given eluate fraction.

[f]A percentage (%) of infective viral particles in each eluate fraction versus the count in the starting viral suspension.

The NTA analysis of the total viral count of both infective and non-infective viral particles showed that the majority of viral particles in the first "flow through" (FT) eluting fraction are non-infective. The latter are practically not bound on the immunoaffinity column.

In contrast, viable (infective) viral particles (>80%) are bound on the column and could be eluted by the mobile phase of an aspect of the present invention.

In this manner the mobile phase from an aspect of the present invention effectively provides separation of infectious from non-infectious viral particles in the suspension; see Table 2.

Thus the mobile phase from an aspect of the present invention which contained 0.75 M L-serine and 0.75 M L-arginine obviously provided significantly better eluting agent than the mobile phase containing only 1.5 M L-arginine from the prior art-like.

In this manner, the mobile phase from an aspect of the present invention gave much better yield of infective viral particles, expressed as $CCID_{50}$, in comparison with the solution from the prior art: 73.0% versus 42.0% (run 3/run 1) and 124.0% versus 77.4% (run 4/run 2).

The Process for Purification and Concentration of Viruses by Immunoaffinity Chromatography by Using the Mobile Phase from an Aspect of the Present Invention The process for virus isolation and purification via immunoaffinity chromatography is consisting of the following steps:
(i) binding the antibody to the chromatographic stationary phase; the antibody is specific for a surface protein of the virus which will be subjected to the said purifying process; the binding is realized by conventional techniques of covalent binding which results in formation of the column for immunoaffinity chromatography;
(ii) then the said chromatographic column from the step (i) is:
  (a) equilibrated by flushing it with the solution of binding buffer consisting of: 20 mM of 3-(N-morpholino) propanesulfonic acid, 0.15 M sodium chloride at pH=7.2-7.4; followed by
  (b) loading of the starting suspension of contaminated viruses which is intended to be purified onto such equilibrated chromatographic column;
(iii) washing of contaminants and non-bound viruses out of the column by flushing it with the same above-mentioned binding buffer;
wherein,
(iv) elution of the purified virus bound on the stationary phase of the column is realized by the use of the elution mobile phase from an aspect of the present invention, yielding an eluate in the form of a suspension of purified virus in said mobile phase.

Thus obtained suspension of purified virus can be subsequently used for further preparation of any conventional type of viral preparations, e.g. viral vaccines, etc, as is known to the person skilled in the art of pharmaceutical technology and biotechnology.

The Use of the Mobile Phase from an Aspect of the Present Invention

The mobile phase according from an aspect of the present invention is employed for purification and/or concentration of viruses by immunoaffinity chromatography in the following manners:
(i) purification from various non-viral impurities such as small or large foreign molecules;
(ii) purification from other viruses; meaning separation from a complex mixture of different viruses;
(iii) separation of infectious from non-infectious viral particles of the same virus; and/or for
(iv) concentration of either infectious or non-infectious viral particles of the same virus.

The viruses that can be subjected to purification and concentration process via immunoaffinity chromatography by using the mobile phase from an aspect of the present invention are shown in Table 3.

TABLE 3

The list of viruses that can be purified by using the mobile phase from an aspect of the present invention via immunoaffinity chromatography.

| No. | Genus | Species | Disease caused by the corresponding virus |
|---|---|---|---|
| | | Family Paramyxoviridae | |
| 1 | Avulavirus | Newcastle disease virus | Avian respiratory disease |
| 2 | Morbillivirus | Measles virus | Measles |
| 3 | Respirovirus | Human parainfluenza virus 1 | Human respiratory disease |
| | | Human parainfluenza virus 3 | Human respiratory disease |
| | | Sendai virus | Avian respiratory disease |
| 4 | Rubulavirus | Human parainfluenza virus 2 | Human respiratory disease |
| | | Human parainfluenza virus 4 | Human respiratory disease |
| | | Mumps virus | Mumps |
| | | Parainfluenza virus 5 | Respiratory disease |
| | | Family Pneumoviridae | |
| 5 | Metapneumovirus | Human metapneumovirus | Human respiratory disease |
| 6 | Orthopneumovirus | Human respiratory syncytial virus | Human respiratory disease |

The mobile phase from an aspect of the present invention is especially suitable for purification of the mumps virus. Due to high immune crossreactivity between different mumps vaccine strains, an aspect of the present invention is fully applicable for purification of all known attenuated mumps virus strains selected from the group comprising: Jeryl Lynn, Urabe, Rubini, Leningrad-Zagreb, Leningrad-3; any newly developed vaccine strain of mumps virus, wild type mumps virus strains, and also their genetically modified counterparts.

Furthermore, due to high similarity in structure between mumps virus and all viruses from the Paramyxoviridae superfamily, an aspect of the invention is applicable for purification of all members of this family of viruses disclosed in Table 3. This encounters vaccine (attenuated) and wild virus strains. For that purpose specific immunoaffinity support should be prepared, containing the antibodies specific for the virus of interest.

Particularly, the inventors found that the methodology is applicable in immunoaffinity chromatography of the viruses selected from the group of all known measles virus vaccine strains selected from the group comprising: AIK-C, Moraten, Rubeovax, Schwarz, Edmonston Zagreb, CAM-70, Changchun-47, Leningrad-4, Shanghai-191, any newly developed vaccine strain of measles virus, wild measles virus strains and their genetically modified counterparts.

Thus, the mobile phase from an aspect of the present invention is preferably used for purification and concentration of the viruses selected from the group consisting of: mumps virus, measles virus, and other viruses from the family of Paramyxoviridae.

In another embodiment of this invention, the mobile phase is employed for purification of infectious from non-infectious viral particles by immunoaffinity chromatography. In this manner, an aspect of the present invention enables preservation of infectivity of viruses what can be hardly achieved by the use of any alternative processes from the state of the art.

Due to the fact that an aspect of the invention is based on universal principle of specific recognition between antigen and antibody and the competitive disruption of bonds between them by amino acid solutions under native conditions, inventors reasonably assume that the methodology is applicable in immunoaffinity chromatography of any antigen-antibody pair.

In additional embodiment of this invention, the mobile phase is employed for purification and/or concentration of viral vectors.

EXAMPLES

General Remarks

For preparation of solutions and buffers, pharmaceutical water for injections was used; further in the text is denoted as "purified water".

All prepared solutions and buffers were filtered through 0.45 μm filter.

Solutions of amino acids L-serine, L-asparagine, and L-glutamine, as well as auxiliary ingredients L-arginine, glycine, and imidazole were prepared by dissolution of respective free amino acids or their salts with pharmaceutically acceptable acids in almost total volume of required purified water. Then the pH values of such obtained solutions were corrected to pH=6.0-8.0, preferably to 7.2-7.4, with pH adjusting agent, acid or base, preferably with either 6 M HCl or 2 M NaOH, followed by addition of purified water up to the total required volume.

All chromatographic procedures were performed on AKTApurifier 100 system equipped with P-900, UV-900 i pH/C-900 (GE Healthcare; Uppsala, Sweden) at room temperature. In all chromatographice experiments the flow was 2 mL/min.

A quantity of ovalbumin was determined by a well known spectroscopic method, see literature reference 18:
18) B. Ehresmann, P. Imbault, J. H. Weil: Spectrophotometric determination of protein concentration in cell extracts containing tRNA's and rRNA's, *Anal. Biochem.* 54 (1973) 454-463, incorporated by reference herein.

Nanoparticle tracking analyses (NTA) were conducted on NanoSight LM10 instrument (Malvern; Worcestershire, UK) equipped with conventional optical microscope, sCMOS camera, and LM10 unit with a red laser ray source. Samples of high concentration were diluted with phosphate buffered saline to $2-8 \cdot 10^8$ particles $mL^{-1}$. Each sample was measured three times and 60 s videos of particles under Brownian motion were recorded and subsequently analyzed with the NTA 3.00068 software. For particle size comparison in our samples, three diameter parameters were used: mean, mode and D90 value, which denotes that 90% of particles have the indicated diameter or smaller. The ratios of the mean, mode and D90 of the examined sample to starting sample were determined, and the average value of these three ratios was taken as the size percentage of the sample in question. The recovery of all virus particles (both infectious and non-infectious) was expressed as the percentage of virus particles found in the experimental sample compared to virus particles found in the starting sample. General knowledge of the NTA method is disclosed in the literature reference 19:
19) B. Carr. M. Wright: *Nanoparticle Tracking Analysis. A review of Applications and Usage* 2010-2012. Nanosight Ltd. (2013), incorporated by reference herein.

Particles size analyses were also measured by using the same NTA method. Samples of high concentration were diluted to working concentrations from $2-8 \cdot 10^8$ particles/mL. Each sample was measured 3 times, and the Brownian motion of the particles in the sample was recorded during 60 seconds, and then analysed with NTA 3.0 0068 software.

Room temperature (r.t.) means the temperature interval of 20-25° C.

Example 1

Immunoaffinity Chromatography of Ovalbumin by Using 1.5 M Arginine Solution at pH=7.3 (Native pH)

Preparation of immunoaffinity stationary phase: Immunoaffinity stationary phase was prepared by binding the rabbit polyclonal antibody of IgG-class specific to ovalbumin to monolithic column (BIA Separations; Ajdovščina, Slovenia).

Polyclonal antibodies were prepared by active immunization of rabbits with ovalbumin (OVA; Serva; Heidelberg, Germany) formulated with adjuvants: Montanide ISA720$^{PGM}$ (Seppic; Puteaux, France) and peptidoglycan monomer (PGM; Pliva; Zagreb, Croatia; see literature references 15-17) as follows: OVA was dissolved in physiological solution (Imunolǒki Zavod; Zagreb, Croatia) in a concentration of 3.78 mg/mL. PGM adjuvant was separately dissolved in physiological solution at a concentration of 7.56 mg/mL. Then, both solutions are combined at volume ratio 1:1 yielding the solution which contained 1.89 mg/mL of OVA and 3.78 mg/mL of PGM. Then, 1 mL of such obtained solution was added in 2.78 mL of Montanide ISA720 adjuvant and homogenized by extruding (10×) of thus obtained mixture through injection syringe 0.9 G20, yielding a stable W-O emulsion with the final concentration of 0.5 mg/mL of OVA and 1 mg/mL of PGM.

Then the rabbits were immunized with 0.5 mL of said emulsion given at two places or with 250 μg of OVA and 500 μg of PGM. The rabbits were immunized 3 times in total, each 4 weeks. Serums were collected 14 days after the third immunization, from which the polyclonal anti-OVA IgG antibodies were isolated for the preparation of immunoaffinity chromatography column.

Said polyclonal antibodies were isolated from the serum of immunized rabbit by chromatography on HiTrap MabSelect Xtra column (GE Healthcare; Uppsala, Sweden) according to the manufacturer's instructions.

For preparation of immunoaffinity column, monolithic "disc-shaped" columns of diameters 1.4 μm and 6 μm and volumes of 0.34 mL and 1 mL were used (BIA Separations; Ajdovščina, Slovenia). The carriers with activated epoxy-groups suitable for antibody binding were employed. This was realized by circulation of an antibody solution at antibody concentration at 3 mg/mL in 0.25 M phosphate buffer of pH=8.0, at room temperature, at the flow of 0.1 mL/min during 48 h. The blocking of remained unreacted epoxy-groups was performed by flushing the column with 1 M solution of ethanolamine at room temperature during 24 h.

The procedure for performing immunoaffinity chromatography: A single immunoaffinity disc of 0.34 mL volume and one 1 mL-immunoaffinity column were serially connected and this served as unitary immunoaffinity stationary phase. The latter was equilibrated by flushing it with 10 column volumes of the binding buffer. The latter was consisting of 20 mM 3-(N-morpholino)propanesulfonic acid, 0.15 M NaCl aqueous solution in purified water at pH=7.3.

Then, to such equilibrated column, the solution of OVA (1 mg/mL in binding buffer) in total of 2 mL was loaded using the 2 mL-loop.

Non-bound OVA was washed by elution of the column with the binding buffer (10 column volumes).

The elution of OVA was realized with 2 mL of 1.5 M solution of Arg (Applichem; Darmstadt, Germany) of pH=7.3 (chromatographic peak E1). The mobile phase solution was previously prepared by dissolution of calculated amount of Arg in purified water followed by correction of pH value with 6 M HCl.

The final step was elution of the column with 2 mL of glycine solution at low pH value (20 mM Gly, 0.15 M NaCl, pH=2.3). During this elution, most of remained quantities of OVA were eluted and registered as chromatographic peak E2.

The chromatographic peaks E1 and E2 were collected manually up to the total consumption of 5 mL of the mobile phase. The experiment was repeated in triplicate.

A quantity of OVA was determined by spectroscopic method according to Ehresmann, by measuring absorbencies at 234.5 nm and 228.5 nm, followed by calculation of the concentration (mg/mL) using the formula as follows: (A228.5 nm-A234.5 nm)×0.3175×dilution; see the section "General remarks" and the literature reference 18.

Since amino acids absorb at these wavelengths by themselves, the eluted peaks were previously liberated from amino acids and the eluted OVA was transferred into 20 mM MOPS buffer, 0.15 M NaCl at pH=7.2 by diafiltration. The latter was conducted by addition of total volume of eluted peak (5 mL) into the ultrafiltration cuvette with pore size 5 kDa (Sartorius; Gottingen, Germany) and diluted to 20 mL with the buffer and subsequently centrifuged at 3,000·g up to 0.2 mL volume. Thus concentrated content was diluted with fresh buffer up to 20 mL and concentrated again down to 0.2 mL again. This procedure was repeated twice. The yield of OVA was 95-100% (as checked by an independent experiment).

The result: The elution of bound OVA with 1.5 M Arg solution at pH 7.3 (native elution) yielded 21.6±4.9 µg ovalbumin (E1) whilst in the second step with acidic Gly solution 41.8±2.76 µg of OVA (E2) was eluted; see Table 1, run 2.

The yield of native elution step was calculated in respect to totally bound (63.4 µg) against the eluted OVA (E1+E2). This total quantity of bound OVA corresponds to total OVA bound on this stationary phase; see Table 1; the last row; as well as from results obtained with Gly solution of low pH, see Table 1, runs 3 and 9.

The yield of native elution of OVA with 1.5 M Arg (pH=7.3) was 34%; see Table 1, run 2.

In the same manner the experiments are performed with:
(i) different L-arginine concentrations: 0.25 M, 0.50 M, 0.75 M, 1.00 M, 1.50 M and 2.00 M; and
(ii) different L-serine concentrations: 1.00 M, 1.50 M, and 2.00 M; the results are presented in FIG. 1.

Example 2

Immunoaffinity Chromatography of Ovalbumin with Native Elution with 0.75 M Ser+0.75 Arg Solution at pH=7.3

The preparation of the immunoaffinity stationary phase, its equilibration with the binding buffer, binding of OVA to the stationary phase, as well as the washing of non-bound OVA were carried out as described in Example 1.

Native elution was performed with 2 mL solution of 0.75 M Ser (Fluka; Buchs, Switzerland)+0.75 M Arg at pH=7.3 (chromatographic peak E1). The mobile phase was previously prepared by dissolution of required amount of Ser and Arg in purified water followed by pH correction to 7.3, according to the instructions described in the section "General remarks".

Final step was the elution with 2 mL of Gly solution of low pH (20 mM Gly, 0.15 M NaCl, pH=2.3) as described in Example 1. The fractions under peaks E1 and E2 were collected up to total volume of 5 mL. The experiment was repeated in triplicate.

The result: The native elution with 0.75 M Ser+0.75 M Arg at pH=7.3 gave 16.8±4.21 µg OVA (peak E1), while in the second step of elution with Gly at low pH, additional 41.8±6.6 µg of OVA (peak E2) was obtained; see Table 1, run 6. The yield of OVA was 29%.

In the same way the experiments are performed with different concentration ranges of Ser+Arg combination:
(i) 0.50 M Ser+0.50 M Arg; and
(ii) 1.00 M Ser+1.00 M Arg;
the results are presented in FIG. 1.

Example 3

Immunoaffinity Chromatography of Ovalbumin by Using Glycine at Low Ph; A Model Elution Under Non-Native Eluting Conditions The preparation of the immunoaffinity stationary phase, its equilibration with the binding buffer, binding of OVA to the stationary phase, as well as the washing of non-bound OVA were carried out as described in Example 1.

In this experiment the elution of bound OVA was conducted with a solution of Gly at low pH value (20 mM Gly, 0.15 M NaCl, pH=2.3). This was performed for evaluation of total bound OVA on the immunoaffinity stationary phase; determination of its capacity. The peak E2 was collected manually from the moment of starting elution, up to the total consumed volume of 5 mL. The experiment was carried out in triplicate.

The result: The elution of OVA with acidic Gly solution, the total of 57.5±5.8 µg ovalbumin (peak E2) was obtained; see Table 1, run 9. This result actually represents a measure of the capacity of this column.

Example 4

Immunoaffinity Chromatography of Mumps Virus Under Native Elution Conditions at pH=7.3 with 1.5 M Arginine Preparation of immunoaffinity stationary phase: Immunoaffinity stationary phase was prepared by binding of guinea pig polyclonal IgG-class antibodies onto the monolithic column (BIA Separations; Ajdovščina, Slovenia).

The polyclonal antibodies were prepared by active immunization of guinea pigs with live attenuated viral vaccine strain L-Zagreb, grown in the culture of Vero cells. These polyclonal antibodies were purified by ultracentrifugation and formulated with adjuvants: Montanide ISA206$^{PGM}$ (Seppic; Puteaux, France) and peptidoglycan monomer (PGM; Pliva; Zagreb, Croatia; see literature references 15-17) according to the procedure described in the Example 1.

These polyclonal antibodies were isolated from the serum of immunized guinea pigs by chromatography on HiTrap MabSelect Xtra column (GE Healthcare; Uppsala, Sweden) according to the manufacturer's instructions. For preparation of immunoaffinity column, monolithic column of 6 μm channel diameter, 6.7 mm of column diameter, 4.2 mm of thickness, and 1 mL of volume (BIA Separations; Ajdovščina, Slovenia) was used.

Stationary phases with active epoxy-groups, suitable for binding the targeted antibodies, were used, according to the manufacturer's instructions. The binding was carried out by circulation of 1 mg/mL antibody solution in 0.25 M phosphate buffer of pH=8.0, at room temperature, at flow of 0.1 mL/min during 48 h. Blocking of remained unreacted epoxy-groups was performed by washing the column with 1 M ethanolamine solution at room temperature during 24 h.

Procedure for immunoaffinity chromatography: Thus prepared immunoaffinity stationary phase with specific mumps virus bound antibodies was equilibrated by washing with 10 column volumes of the binding buffer consisting of 20 mM 3-(N-morpholino)propanesulfonic acid, 0.15 M NaCl of pH=7.3.

The mumps viral suspension was prepared by replication of the viral vaccine strain L-Zagreb in the Vero cell culture. After the cultivation, the suspension was filtered through 0.45 μm filter yielding the filtrate. The latter contained 10.008 log $CCID_{50}$ viruses (what is a measure of quantity of infective viruses), or $1.17 \cdot 10^{13}$ of total viral particles as determined by the NTA method; see section "General remarks".

Thus obtained virus suspension (70 mL) was added onto previously prepared immunoaffinity column using the superloop. During the addition of the viral suspension, a "flow through" (FT) fraction was collected in two parts: 50 mL (as FT1) and 20 mL (as FT2). Non-bound, virus was eluated by flushing with 10 volumes of the column with the binding buffer solution.

Native elution at pH=7.3 according to this invention was carried out by elution with 1.5 M aqueous L-arginine solution. This mobile phase was previously prepared by dissolution of corresponding amounts of L-arginine (Applichem; Darmstadt, Germany) in purified water with correction of pH value with 6 M aqueous HCl solution.

Then the column was eluted with 2 mL of 2 M aqueous NaCl solution.

Moreover, the final elution of bound viruses was preformed by washing the column with 2 mL of 20 mL glycine, 0.15 M NaCl aqueous solution at non-native pH value of 2.3, what is usual effective way of eluting molecules in immunoaffinity chromatography.

Thus, the eluates which correspond to the chromatographic peaks E1, E2, and E3 were collected manually: E1 from the starting point of using the mobile phase to the total volume of 6.5 mL, E2 for further 5 mL, and E3 for additional 4 mL.

The efficacy (or yield) of the chromatographic process was estimated by the test for quantification of infective viral particles, so called, determination a half of cell culture infective dose ($CCID_{50}$) and quantification test for total viral particles by nanoparticle tracking analysis (NTA). The yield of respective elution steps was expressed against the total amount of virus bound onto the stationary phase of the column.

The result: By native elution with 1.5 M aqueous L-arginine solution at pH=7.3, 9.631 log $CCID_{50}$ was eluted, followed by 7.925 log $CCID_{50}$ (100× times less) in the next step with 2 M aqueous NaCl solution, and finally 7.242 log $CCID_{50}$ in the last step at pH=2.3 (see Table 2, run 1).

The yield in the native elution step was 42% (Table 2, run 1), whilst collected eluates E2 and E3 contained less than 1% of infective virus. Small amount of virus was detected in the FT fractions (9.2%) what means that this part of the starting material did not bind to the stationary phase of the column.

Total yield of the whole process was 52.2% what clearly suggests that a large part of infective viral particles was lost during the chromatographic process due to, so called, shear stress. The NTA analysis of the total viral particles showed that 46% of starting virus particles were not bound on the column at all, but were just passed out into the fractions FT1 and FT2. The 1.5 M aqueous solution of L-arginine eluted 32.8% of total viral particles, whereas E2 contained 3.9% and E3 2.4% of the latter; see Table 2, run 1.

Such result strongly suggests that this chromatographic process effectively separates infectious from non-infectious viral particles, providing enrichment of virus suspension. Thus infectious viral particles are bound more readily than non-infectious ones. In other words, non-infectious particles just passed through the column and finished in the FT fractions, whilst the infectious ones were bound onto the column and subsequently eluted with the mobile phase yielding the eluate enriched with infectious virus.

In numbers, the ratio of infective virus, $CCID_{50}$/total virus (NTA result), in the starting suspension before the chromatographic process was 0.060. After the chromatographic process this ratio was 0.111, what represents the increase for 1.86 times. The same ratio in the FT fraction was decreased down to 0.016, what shows its enrichment in non-infectious viral particles, because the infectious ones remained bound onto the column.

The analysis of the particles size in the fractions of the chromatographic process shows that the non-infectious particles in the FT fraction were smaller for 25% against the average particles size from the starting viral suspension. Probable cause of this result is a lack of antigenic determinants on the virus surface in these viral particles what is the reason why these could not bind to the antibodies from the chromatographic column.

The results for the mobile phase containing 1.5 M Arg are presented in Table 2, runs 1 and 2.

Example 5

Immunoaffinity Chromatography of Mumps Virus with 0.75 M Serine and 0.75 Arginine Solution at Native Eluting Conditions (pH=7.3) According an Aspect of the Present Invention The preparation of immunoaffinity stationary phase, its equilibration with the binding buffer, as well as addition of the mumps virus suspension was performed as described in the Example 4.

To such prepared column, 70 mL of the viral suspension containing 9.613 log $CCID_{50}$ viruses (a measure of amount of infectious virus) or $1.464 \cdot 10^{11}$ of total viral particles, as determined by the NTA method, was added.

During the sample addition, the "flow through" (FT) fraction was collected into two parts; the first one of 50 mL (FT1) and the second one of 20 mL (FT2). Native elution was carried out with previously prepared solution of the mobile phase from an aspect of the present invention consisting of 0.75 M L-serine and 0.75 M L-arginine aqueous solution with corrected pH value to 7.3 by using 6 M HCl. During the elution phase, 6 mL of eluting fraction E1 was collected.

In the next step, as described in the Example 4, the column was eluted with 2 mL of 2 M NaCl solution yielding the 5 mL of eluate characterized by the chromatographic peak E2.

The last step includes the elution with 2 mL of glycine solution (pH=2.3), as explained in the Example 4, giving 4 mL of the fraction E3.

The efficiency (the yield) of the chromatographic process is assessed as defined in the Example 4.

The result: Elution at native conditions (pH=7.3) with 0.75 M Ser+0.75 M Arg solution yielded 9,476 log $CCID_{50}$, whereas in the next step with 2 M NaCl, 8,323 log $CCID_{50}$ of viral particles. In the final eluting step under non-native conditions (pH=2.3) the amount of infectious viruses was not determined. However, due to harsh eluting conditions, no infective virus is expected at this very low pH conditions; see Table 2, run 3.

The yield of the native elution (pH=7.3) with the mobile phase of an aspect of the present invention consisting of 0.75 M Ser+0.75 M Arg was 73% (Table 2, run 3), whilst in the eluent E2 the yield of infective virus was 5%. A small amount (11.5%) of virus was observed in the FT fractions, similarly as in the Example 4.

A total yield of the whole process was 89.6%. The analysis of total particle concentration by NTA (both infective and non-infective) showed that 38.8% of all viral particles were not bound onto the column, but just passed through and were collected into the FT1 and FT2 fractions.

The mobile phase of an aspect of the present invention consisting 0.75 M Ser+0.75 M Arg at pH=7.3 was able to elute 25.1% of all viral particles, whereas in the E2 fraction, the yield was only 2.4% and in E3 fraction 2.1%; see Table 2, run 3.

Once again, such results suggest that this chromatographic process effectively separates the infectious from non-infectious viral particles. The former ones are more readily bound onto the stationary phase of the column, whilst the latter ones just passed through the column without binding and were collected in the FT fractions. Thus only the bound infectious viral particles are predominately eluted with the mobile phase of an aspect of the present invention.

The ratio of infectious virus ($CCID_{50}$)/total viral amount (from NTA method) in the starting viral suspension was 0.028, whereas in the eluting fraction obtained with the mobile phase from an aspect of the present invention the ratio was 0.082, what represents the enrichment for 2.91x.

In the same time, the same ratio in the FT fractions decreased to 0.009.

Also, the particles size analysis shows that the non-infectious viruses from the FT fractions were 15% smaller than were average viral particles from the starting suspension. The explanation of this phenomenon is elucidated in Example 4.

Figure 2:
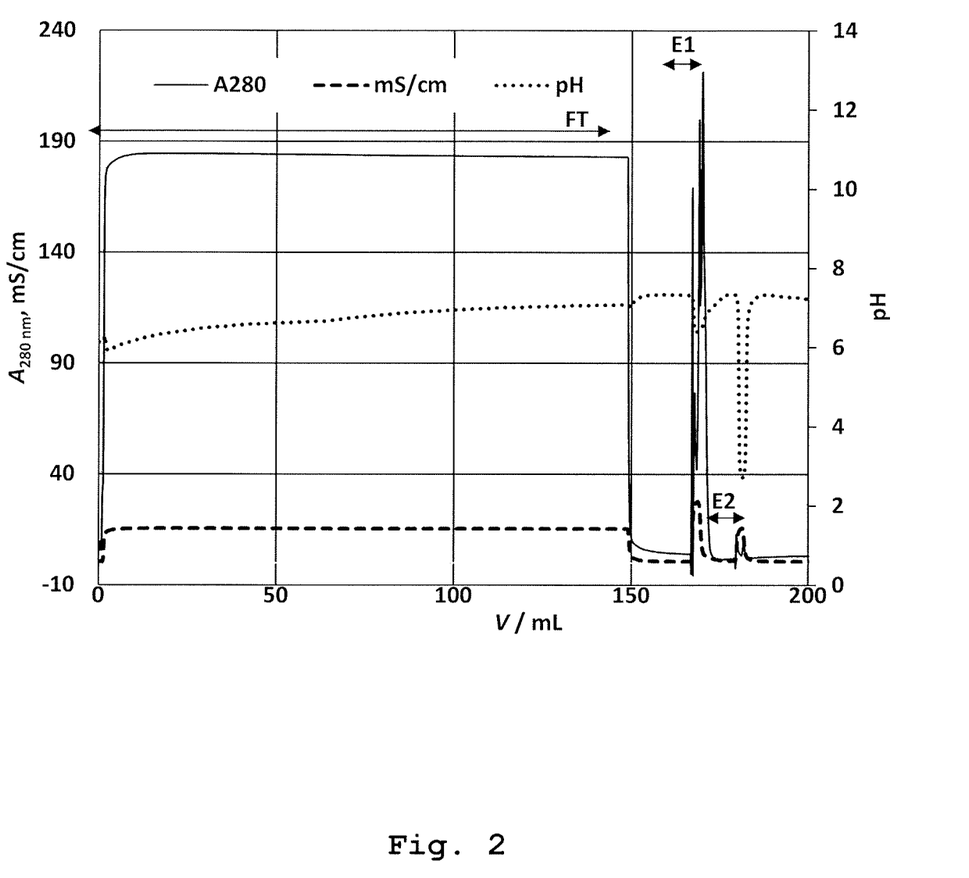
FIG. 2: Shows a typical chromatogram obtained by immunoaffinity chromatography of the mumps virus. 150 mL of mumps virus sample was loaded and eluted with: E1; 0.75 M arginine (Arg)/0.75 M serine (Ser), pH=7.3; and E2; 20 mM glycine (Gly), 0.15 M NaCl, pH=2.3. F=2 mL/min. Binding buffer; 20 mM MOPS, pH 7.3. FT stands for "flow through" fraction, a material dissolved and/or suspended in the starting viral suspension which is entered onto the prepared immunoaffinity chromatography column, and flows through the column with the eluate, essentially without binding.

The results for the use of the mobile phase based on L-serine and L-arginine are presented in Table 2, runs 3 and 4; and in FIG. 2.

CONCLUSION

An aspect of the present invention discloses the new composition of the elution mobile phase for effective purification and concentration of viruses by immunoaffinity chromatography.

The elution mobile phase from an aspect of the present invention provides significantly more efficient purification and concentration in comparison with the eluents from the prior art based on arginine or imidazole at acidic pH=2.0-4.0; see literature reference 11.

Important additional feature of an aspect of the present invention is a possibility to perform such kind of purification which involves separation and thus concentration of infectious or non-infectious viruses from their mixture.

In this manner, thanks to its high efficacy, the process according to an aspect of the present invention enables purification of infectious viruses.

In additional embodiment of this invention, the ingredients of the mobile phase such as amino acids L-serine (1), L-asparagine (2), and L-glutamine (3), as well as auxiliary ingredients L-arginine, glycine or imidazole are all pharmaceutically-acceptable ingredients which are, in the same time, also known to be vaccine stabilizing agents. This provides possibility of direct use of thus obtained viral eluates (suspensions) for manufacturing of vaccines, without necessary removal of purification reagents as is the case in several existing chromatographic processes.

INDUSTRIAL APPLICABILITY

An aspect of the present invention involves the novel composition of the mobile phase for immunoaffinity chromatography, the process for conducting said chromatographic process, and the use of the mobile phase in production of purified viruses. Thus the industrial applicability of an aspect of the present invention is obvious.

LIST OF ABBREVIATIONS

Arg—L-arginine
Asn—L-asparagine
FT—"Flow through"—stands for a material dissolved and/or suspended in the starting viral suspension which is entered onto the prepared immunoaffinity chromatography column, and flows through with the eluate essentially without binding.
Gln—L-glutamine
Gly—glycine
HEPES—2-[4-(2-hydroxyethyl)piperazine-1-yl]-ethanesulfonic acid (buffer)
Imi—imidazole
M—molar concentration (molarity) [mol/dm$^3$]
MES—2-(N-morpholino)ethanesulfonic acid (buffer)
MOPS—3-(N-morpholino)propanesulfonic acid (buffer)
OVA—ovalbumin (a model protein)
PIPES—piperazine-N,N'-bis(2-ethanesulfonic acid) (buffer)
Ser—L-serine
TAPSO—2-hydroxy-3-[tris(hydroxymethyl)methylamino]-1-propane sulfonic acid (buffer)
TES—N-[tris(hydroxymethyl)methyl]-2-aminoethane sulfonic acid (buffer)
Tricine—N-[tris(hydroxymethyl)methyl]glycine (buffer)
Tris—tris(hydroxymethyl)methylamine (Tris)

The invention claimed is:

1. A process for virus isolation and purification via immunoaffinity chromatography wherein the process comprises:
   (i) binding an antibody to a chromatographic stationary phase; the antibody is specific for a surface protein of the virus which will be subjected to the purifying process; the binding is realized by covalent binding which results in formation of the column for immunoaffinity chromatography;
   (ii) then the chromatographic column from the step (i) is:
      (a) equilibrated by flushing it with a solution of binding buffer consisting of: 20 mM of 3-(N-morpholino) propanesulfonic acid, 0.15 M sodium chloride at pH=7.2-7.4; followed by
      (b) loading of the starting suspension of contaminated viruses which is intended to be purified onto such equilibrated chromatographic column;
   (iii) washing of contaminants and non-bonded viruses out of the column by flushing it with the same binding buffer from the step (ii); and
   (iv) the elution of the purified virus bounded on the stationary phase of the column is realized by the use of a mobile phase for elution in the immunoaffinity chromatography of viruses that is a solution comprising:
      (a) one or more amino acids;
      (b) one or more ingredients: L-arginine, glycine, imidazole, or their salts with pharmaceutically acceptable acids;
      (c) one or more pharmaceutically acceptable pH adjusting agents, acid or base, for correcting the pH value of the mobile phase to pH=6.0-8.0; and
      (d) purified water; up to 100% w/w of the mobile phase composition;
         wherein the amino acids (i) are selected from the group consisting of: L-serine <1>, L-asparagine <2>, L-glutamine <3>, or their salts with pharmaceutically acceptable acids, yielding an eluate in the form of a suspension of purified virus in said mobile phase.

2. A method for purification of viruses by using a mobile phase for elution in immunoaffinity chromatography of viruses that is a solution comprising:
   (i) one or more amino acids;
   (ii) one or more ingredients: L-arginine, glycine, imidazole, or their salts with pharmaceutically acceptable acids;
   (iii) one or more pharmaceutically acceptable pH adjusting agents, acid or base, for correcting the pH value of the mobile phase to pH=6.0-8.0; and
   (iv) purified water; up to 100% w/w of the mobile phase composition;
   wherein the amino acids (i) are selected from the group consisting of: L-serine <1>, L-asparagine <2>, L-glutamine <3>, or their salts with pharmaceutically acceptable acids.

3. The method according to claim 2 for purification of infectious from non-infectious viral particles by immunoaffinity chromatography.

4. The method according to claim 2 for purification of viruses selected from the group consisting of:
   (a) Avulaviruses;
   (b) Morbilliviruses;
   (c) Respiroviruses;
   (d) Rubulaviruses;
   (e) Metapneumoviruses; and
   (f) Orthopneumoviruses.

5. The method according to claim 4, wherein the viruses are selected from the group consisting of: mumps virus, measles virus, and viruses from the family of Paramyxoviridae.

6. The method according to claim 2, for purification and/or concentration of viral vectors.

7. The method according to claim 2 for purification of viruses selected from the group consisting of:
   (a) Newcastle disease virus;
   (b) Measles virus;
   (c) Human parainfluenza virus 1;
   (d) Human parainfluenza virus 3;
   (e) Sendai virus;
   (f) Human parainfluenza virus 2;
   (g) Human parainfluenza virus 4;
   (h) Mumps virus;
   (i) Parainfluenza virus 5;
   (j) Human metapneumovirus; and
   (k) Human respiratory syncytial virus.

* * * * *